(12) United States Patent
Vilsmeier et al.

(10) Patent No.: US 6,223,067 B1
(45) Date of Patent: Apr. 24, 2001

(54) REFERENCING DEVICE INCLUDING MOUTHPIECE

(75) Inventors: Stefan Vilsmeier, Poing; Rainer Birkenbach, Feldkirchen, both of (DE)

(73) Assignee: Brainlab Med. Computersysteme GmbH, Heimstetten (DE)

( * ) Notice: Subject to any disclaimer, the term of this patent is extended or adjusted under 35 U.S.C. 154(b) by 0 days.

(21) Appl. No.: 09/056,450

(22) Filed: Apr. 7, 1998

(30) Foreign Application Priority Data

Apr. 11, 1997 (DE) ............................................. 197 15 202

(51) Int. Cl.$^7$ ........................................................ A61B 5/05
(52) U.S. Cl. ........................... 600/426; 606/130; 378/170; 378/205
(58) Field of Search ................................... 600/426, 424, 600/407, 415, 417, 429; 606/130; 378/204–206, 170

(56) References Cited

U.S. PATENT DOCUMENTS

| 4,841,965 | * | 6/1989 | Jacobs | 378/208 |
| 4,971,060 | * | 11/1990 | Schneidert et al. | 600/407 |
| 5,090,047 | * | 2/1992 | Angotti et al. | 378/170 |
| 5,230,623 | * | 7/1993 | Guthrie et al. | 433/72 |
| 5,531,229 | * | 7/1996 | Dean et al. | 606/130 |
| 5,588,430 | * | 12/1996 | Bova et al. | 600/407 |
| 5,706,811 | * | 1/1998 | Takeda et al. | 600/407 |
| 5,797,924 | * | 8/1998 | Schulte et al. | 606/130 |
| 5,947,981 | * | 9/1999 | Cosman | 606/130 |

FOREIGN PATENT DOCUMENTS 19 619 761
A1      7/1970  (DE) .

* cited by examiner

*Primary Examiner*—Brian L. Casler
(74) *Attorney, Agent, or Firm*—Renner, Otto, Boisselle & Sklar LLP

(57) ABSTRACT

The invention relates to a referencing device for mapping the position of bodily surgical or examination target points comprising at least three reflectors, the position of which can be localized by a computer-assisted position tracking and/or a CT scan, and an adapter connected to the reflectors, by means of which the referencing device is attachable to a part of the body wherein the adapter comprises a mouthpiece securable to the upper jaw by means of vacuum pressure. The invention relates furthermore to a method for referencing bodily surgical or examination target points. The device in accordance with the invention is employed more particularly in radiotherapy and in neurosurgery.

3 Claims, 1 Drawing Sheet

REFERENCING DEVICE INCLUDING MOUTHPIECE

BACKGROUND OF THE INVENTION

1. Field of the Invention

The invention relates to a referencing device for mapping the position of bodily surgical or examination target points comprising at least three reflectors, the position of which can be localized by a computer-assisted position tracking and/or a CT scan, and an adapter connected to the reflectors, by means of which the referencing device is attachable to a part of the body, wherein said adapter comprises a mouthpiece securable to said upper jaw by means of vacuum pressure.

The invention relates furthermore to a method for referencing bodily surgical or examination target points. The device in accordance with the invention is employed in radiotherapy and neurosurgery.

2. Description of the Prior Art

Referencing devices which make visible the current position of the patent as well as the three-dimensional position of surgical instruments and hardware on a computer monitor or which contribute towards directly mapping positions in radiosurgery are known. They serve to reference the anatomical data obtained for example by a CT scan in a fiducial system, i.e. permitting three-dimensional assignment of the patient anatomy to the referencing device in each case which in turn can be tracked by a position tracking system for monitoring in the operating room. Position tracking systems of this kind comprise for example an infrared emitter and two infrared cameras which "see" the three-dimensional position of reflectors attached to the patient or to the surgical instruments and hardware. In this arrangement a computer assigned to the position tracking facility computes from the information on the reflector position the up-dated or current position of the patient as well as that of the surgical instruments and hardware and assigns this information to the patient data from the CT scan thus making image-assisted navigation in the operating room or computer-assisted radiotherapy possible.

To enable the anatomy of the patient as established from the CT scan in the above systems to be mapped as precisely as possible artifical landmarks are attached to the patient prior to scanning, the images of which are mapped in the CT. In actual surgery the positions of such landmarks are tracked by a position tracking system as described above, for instance, and thus due to the fixed assignment of the patient anatomy to the position of the landmarks the current position of the surgery target points is also known via the known position of the landmarks.

The landmarks can be principally attached to the patient invasively or non-invasively. Invasive methods of attachment, for example, trephining and securing the landmarks in the holes are highly accurate but extremely stress the patient. Noninvasive methods involve, for example, attaching the landmarks to the skin by means of surgical plaster. The drawback here is that the skin is prone to being slightly shifted which in a worst case condition may amount to a few centimeters resulting in position tracking with such bonded landmarks being inaccurate.

Known from German Patent 19 619 761 A1 is a locating device for the human head in which an upper jaw impression mold is applied to the patient which can be affixed to the upper jaw by vacuum pressure. Applying this upper jaw impression mold in the mouth of the patient merely serves to precisely locate the head of the patient; however, the upper jaw impression mold for locating the head is totally rigid and unmovable in use.

SUMMARY OF THE INVENTION

It is the object of the present invention to provide a referencing device for mapping the position of bodily surgical or examination target points featuring high positional fidelity, it also being an object to provide a corresponding referencing method.

This object is achieved in accordance with the invention by the adapter, by means of which the referencing device can be applied to a part of the body, comprising a mouthpiece attachable to the upper jaw by vacuum pressure.

The advantage of the present invention lies particularly in the possibility of referencing surgery target points precisely reproducible without excessive patient stressing. Securing the adapter and thus the reflectors via a mouthpiece to the upper jaw allows high position fidelity every time the mouthpiece is returned in place due to the characteristical shape or each upper jaw or dental impression of the patient. This means that the reflectors attached to the mouthpiece can be relocated highly accurately in the same spacing and locational relationship to the patient anatomy every time the referencing device is returned in place.

Having to put up with a major displacement as is the case with landmarks attached to the skin is now obviated.

In addition, locating the mouthpiece by vacuum pressure is relatively pleasant for the patient and although the attachment is sufficiently rigid it can be released at any time without any injury to the patient.

In one advantagous aspect the adapter comprises an upper jaw impression mold which is filled with a settable impression compound. This known impression mold permits relatively fast and highly accurate modelling of an upper jaw or dental impression. Such an upper jaw impression mold can be reinserted in the mouth of the patient at any time in a reproducible location, the upper jaw impression mold preferably covering the dental area and the hard palate of the upper jaw.

A dental impression provides a highly characteristical anatomical image of the patient for reproducible attachment. When, in addition, an impression of the hard palate is made this enhances, on the one hand, the stability with which the mouthpiece is secured to the patient and, on the other, opens up the possibility of making use of the mouthpiece also in the case of patients having no teeth (due to age or an accident).

In a preferred embodiment of the referencing device in accordance with the invention scallops are provided in the surface region of the set impression compound which leave an air space between the hard palate and the surface of the impression compound with the mouthpiece in place, this air space permitting a vacuum pressure to be applied. Due to such an air space which may be produced, for example, by implanting an insert in the impression compound during setting, the possibility of vacuum pressure securement is easily created. When the air space is brought into connection outwardly with a vacuum pump the air can be exhausted from the air space with the mouthpiece in place, as a result of which the mouthpiece comes into intimate, firm contact with the upper jaw.

Preferably the reflectors of the referencing device are removably appliable in a characteristic array.

Removable reflectors permit, on the one hand, the facilitated replacement of the reflectors for a CT scan by the reflectors which can be localized by a navigational means in the operating room, they on the other hand permitting simple means of sterilization at no great expense by presterilized reflectors being applied, for example, just before commencement of an operation.

A characteristic reflector array existing only on the mouthpiece enables the navigating means in the operating room to explicitly differentiate this reflector array from other reflector arrays (for example on surgical instruments and hardware), here too, it being possible to explicitly assign the location of the surgery target relative to the characteristic reflector array on the mouthpiece.

In the method in accordance with the invention for referencing bodily surgical or examination target points the position of at least three reflectors is tracked by computer-assisted position tracking and/or a CT scan whereby the reflectors are attached by means of an adapter to the part of the body concerned. The referencing device is secured via a mouthpiece serving as the adapter and locatable on the upper jaw by means of vacuum pressure.

The method in accordance with the invention can be implemented with all of the embodiments of the referencing means as discussed above.

The invention relates also to the use of a referencing means configured in accordance with the aspects as described in the current position mapping or updating radiotherapy target point data.

In radiotherapy at least the parts of the body to be irradiated need to fixed in place. This requirement is satisfied, for example in the case of brain tumor irradiation, by locating the head in a mask adapted to the shape of the head, this mask in turn being securely attached via a head ring to the radiation bench on which the patient is located.

Radiosurgery target point localization can then be done, on the one hand, by the patient being integrated together with his locating means in a neuronavigation system as described above for the operating room, i.e. the positions of the surgical instruments and hardware and, via the referencing means, also the patient anatomy are each signalled to a computer system which then controls the irradiation means. Conventionally for this purpose reflectors or active emitter means for signalling the position are applied to the surgical instruments and hardware, for example, to the head ring of the mask. Although a locating mask for the head of the patient permits a relatively accurate localization it principally surrounds the scalp of the patient as a result of which shifts in location may occur.

To solve this problem a referencing means in accordance with the invention may be secured to the patient via a mouthpiece. As already described above, the location of the radiosurgical target points, for example a brain tumor, is known with high accuracy via the referencing means with the reflectors in the navigation system of the operation room, this being the reason why also any shift in position of the head within the mask can be corrected in accordance with the invention by such a shift being detected by the reflectors of the referencing means and signalled to the computer system. The up-dated position of the radiosurgery target point is thus also still precisely known even after such a shift and the irradiation can thus be adapted to the up-dated target data such that the patient bench together with the patient are corrected in position so that the irradiation beam relocates at the slightly shifted radiosurgery target point.

A second basic possibility of mapping radiosurgery target points consists in providing above the part of the patient's body requiring radiosurgery a frame, to the outer walls of which optical target point mapping aids are attached. Thus, for example, in one known application a roughly cuboidal frame is secured about the head of the patient, the side surface areas of the cube being covered with films on which the contour of a tumor in the corresponding section plane as well as the radiosurgery centerpoint are marked. The beam is focussed on the radiosurgery target point via these target aids.

Although in this mode of radiosurgery the head of the patient is located in place, shifts in position may occur via the scalp when located in place non-invasively, i.e. due to this shift the problem exists of the films no longer precisely indicating after the shift the radiosurgery target point.

This problem is solved in turn by employing a referencing means in accordance with the invention on a mouthpiece so that the changed position or the up-dated position of the reflectors in each case can be mapped by a position tracking in the operating room via the reflectors. Since the position of the radiosurgery target point relative to the reflectors is precisely known from the CT scan in which the mouthpiece was already secured to the referencing device on the patient, new films can now be printed with the information received as to the shift in position which in turn define the current position of the radiosurgery target point three-dimensionally, i.e. relative to the frame. The films formerly in the frame can be replaced relatively simply by the new ones so that correct up-dated target point localization in radiosurgery is made possible.

A further possibility of making use of the referencing device in accordance with the invention as already indicated is in CT scan-assisted neurosurgery with the aid of a position tracking means serving as neuronavigation, the procedure in this case being briefly outlined as follows: the mouthpiece with its soft impression compound is adapted to the upper jaw of the patient; once the impression compound has set the mouthpiece can be removed from the upper jaw of the patient and then the reflectors can be secured to the mouthpiece.

For the CT scan the mouthpiece is reinserted and located in place, whereby reflectors are employed by means of which the CT scans can be mapped, the patient anatomy as well as the position of the reflectors relative to this anatomy then being mapped by a CT scan data set.

After the CT scan the mouthpiece can be removed without difficulty from the patient, to be later returned in place with the referencing device in subsequent neurosurgery. The reflectors firstly employed may be configured funnel-shaped, the apex of which is located precisely at the centerpoint of the reflectors. The position tracking system in the operating room "sees", on the one hand, the characteristic reflector array for the referencing device on the mouthpiece whilst the possibility continues to exist of signalling the individual reflectors by their funnel apex with a cursor instrument which signals the position tracking system the precise location of the referencing device in the operating room.

There is then in turn the possibility of replacing the funnel-shaped reflectors by globular reflectors which can be tracked very well by the position tracking means.

During the subsequent operation the current location of the patient anatomy, i.e. including the surgery target point, is known at all times via the reflectors. Tracking the position in this way is highly precise due to the accurate and reproducible securement of the mouthpiece so that an operation assisted by the neuronavigation system can be implemented with high precision.

BRIEF DESCRIPTION OF THE DRAWINGS

A referencing device in accordance with the invention will now be explained with reference to the annexed Figures in which.

DETAILED DESCRIPTION OF THE PREFERRED EMBODIMENTS

Figure 1:
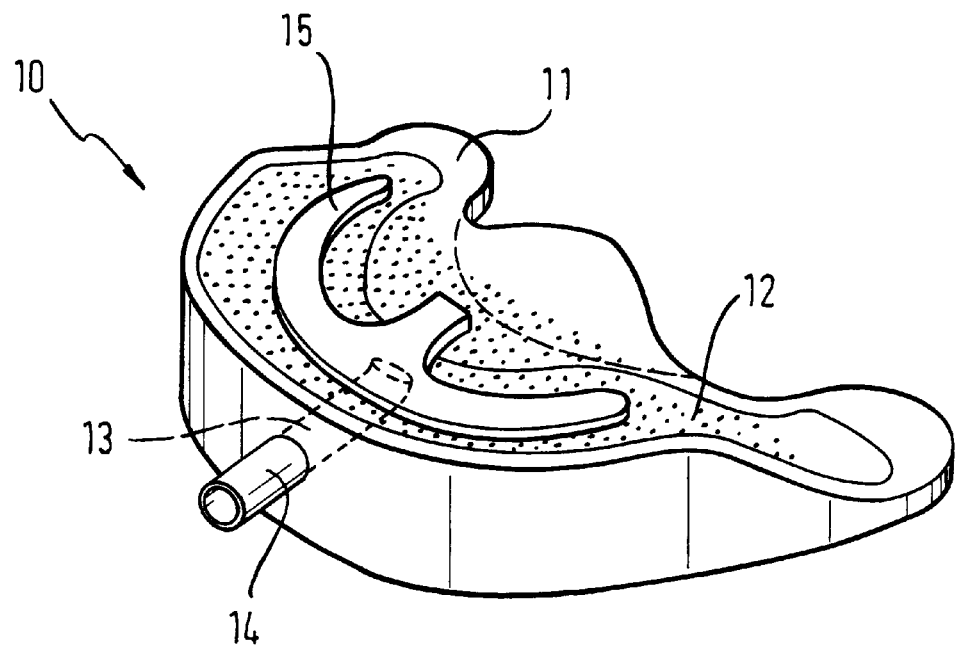
FIG. 1 illustrates a mouthpiece for the referencing device in accordance with the invention.

Referring now to FIG. 1 there is illustrated the mouthpiece identified as a an upper jaw impression compound 12. This impression compound 12 sets after first-time application of the upper jaw mold 11 on the patient, it then bearing an impression of the upper jaw. Prior to first-time application to the upper jaw a soft rubber plate 15 contoured roughly as shown in FIG. 1 is placed on the impression compound 12. An air passage 13 ending at the rubber plate is continued outwards at the upper jaw mold 11 by a connecting passage 14.

Once the impression compound 12 has set the plate 15 can be removed from the compound 12, as a result of which a scallop materializes, forming an air space. When the mouthpiece 10 is then applied in the set condition to the upper jaw of the patient, air can be exhausted from the air space by connecting it to a vacuum pump, as a result of which the mouthpiece 10 is affixed to the upper jaw of the patient.

Figure 2:
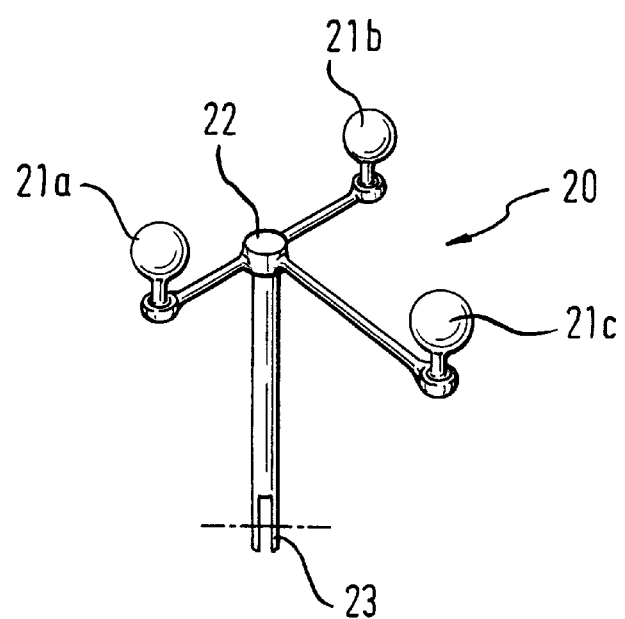
FIG. 2 illustrates a reflector applicable to the mouthpiece.

Referring now to FIG. 2 there is illustrated a reflector 20 comprising a three-armed support 22, to which the three reflectors 21a, 21b, 21c are secured, and a mount 23 depicted schematically. The mount 23 can be adapted in each case to the shape and means of securing the mouthpiece. The reflectors 21a, 21b, 21c are removably attached to the end sections of the arms of the support 22, whereby, as already described, suitable reflectors are attachable for each phase of the operation. The reflectors 21a, 21b, 21c are attached in a characteristic array exclusively assigned in each case by position tracking to the referencing device in accordance with the invention.

The support 23 depicted schematically can be adapted in length and configuration to each operating situation or the fastening means on the mouthpiece 10. It is of particular advantage that due to a suitable configuration and application of the support 23 the reflector array 21a, 21b, 21c can be brought out from the operating site to such an extent that it poses no obstruction to the operating physician or to the beam path of the radiosurgery system.

It is basically possible by means of the referencing device comprising the mouthpiece 10 and reflector 20 to precisely localize a patient and his anatomy three-dimensionally at any time also without affixing.

What is claimed is:

1. A referencing device for mapping a position of bodily surgical or examination target points, comprising
   a) at least three reflectors for enabling position localizing thereof by at least one of a computer-assisted position tracking system and a CT scan, and
   b) an adapter connected to said reflectors, and wherein
   c) said adapter comprises a mouthpiece securable to an upper jaw of a patient by means of vacuum pressure, and said adapter includes a connecting passage for connecting to a source of vacuum, and wherein:
      said adapter comprises an upper jaw impression mold which is filled with a settable jaw impression compound,
      a surface region of said impression compound has placed therein a removable member which when removed from said mouthpiece leaves an air space between said hard palate and said surface of said impression compound which can be subjected to a vacuum pressure, and
      said air space is connected to said connecting passage.

2. The referencing device as set forth in claim 1, wherein said upper jaw impression mold is configured to cover the dental area and the hard palate of the upper jaw.

3. The referencing device as set forth in claim 1, wherein said reflectors are removable from said adapter.

* * * * *